(12) United States Patent
Lin et al.

(10) Patent No.: US 10,808,063 B2
(45) Date of Patent: Oct. 20, 2020

(54) PHOTOPOLYMER COMPOSITION AND APPLICATION THEREOF

(71) Applicant: NATIONAL YANG-MING UNIVERSITY, Taipei (TW)

(72) Inventors: Yuan-Min Lin, Taipei (TW); Jiun-Ming Su, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 213 days.

(21) Appl. No.: 15/829,437

(22) Filed: Dec. 1, 2017

(65) Prior Publication Data

US 2019/0119429 A1    Apr. 25, 2019

(30) Foreign Application Priority Data

Oct. 19, 2017  (TW) .............................. 106135956 A

(51) Int. Cl.

| | | |
|---|---|---|
| *C08F 289/00* | (2006.01) | |
| *A61L 27/22* | (2006.01) | |
| *A61L 27/52* | (2006.01) | |
| *A61L 27/58* | (2006.01) | |
| *C12N 5/00* | (2006.01) | |
| *A61L 27/54* | (2006.01) | |
| *A61L 27/50* | (2006.01) | |
| *A61L 27/46* | (2006.01) | |

(52) U.S. Cl.
CPC .......... *C08F 289/00* (2013.01); *A61L 27/222* (2013.01); *A61L 27/46* (2013.01); *A61L 27/50* (2013.01); *A61L 27/52* (2013.01); *A61L 27/54* (2013.01); *A61L 27/58* (2013.01); *C12N 5/0062* (2013.01); *C12N 2513/00* (2013.01); *C12N 2529/10* (2013.01); *C12N 2533/30* (2013.01); *C12N 2533/54* (2013.01); *C12N 2537/10* (2013.01)

(58) Field of Classification Search
None
See application file for complete search history.

*Primary Examiner* — Heidi Reese
(74) *Attorney, Agent, or Firm* — Muncy, Geissler, Olds & Lowe, PC

(57) ABSTRACT

The present disclosure provides a photopolymer composition and the applications thereof. The photopolymer composition comprises: 5 weight percent to 15 weight percent of gelatin methacrylate (GelMA), 0.1 weight percent to 5 weight percent of silanized biologically active additive, 0.1 weight percent to 5 weight percent of photoinitiator, and 75 weight percent to 95 weight percent of a solvent. Compared to a conventional hydrogel, the hydrogel prepared from the photopolymer composition of the present disclosure has improved compressive strength, mechanical strength and stability. Accordingly, the hydrogel is applicable to biomedical research and tissue repair.

13 Claims, 10 Drawing Sheets

PHOTOPOLYMER COMPOSITION AND APPLICATION THEREOF

BACKGROUND OF THE INVENTION

Technical Field of the Invention

The present disclosure relates to a photopolymer composition, and particularly relates to a photopolymer composition applicable to cell culture, tissue regeneration and tissue repair after formation.

Background

Tissue engineering is a kind of regenerative medicine, which refers to the combination of clinical medicine, biological science, and materials engineering to produce functional cells or tissues in vitro. The functional cells or tissues repair or replace the tissues to restore the aging or damaged tissues or organs in the body. For tissue engineering, cells, scaffolds and bio-signaling molecules are three major factors to determine the effectiveness of tissue regeneration.

The selection of bio-signaling molecules is determined by the cells or tissues to be prepared. For example, in order to avoid immune rejection, cells are mostly derived from the autologous cells from the human body, which are stem cells with differentiation ability, such as mesenchymal stem cells. The stem cells are co-cultured with specific bio-signaling molecules to induce the cells to begin signaling transduction, which drives the stem cell to differentiate into cells in specific tissue. Until now, the knowledge of culture and isolation of stem cell and the knowledge of bio-signaling molecules have been well developed. For scaffold, which provides the cell an environment to grow, relatively speaking, since factors such as the biocompatibility, cell adhesion, and cytotoxicity of the scaffold affects cell growth, which further affects the results of tissue preparation and tissue regeneration, the researchers in this field are still studying and improving the scaffold.

The selection of bio-signaling molecules is determined by the cells or tissues to be prepared. For example, in order to avoid immune rejection, cells are mostly derived from the autologous cells from the human body, which are stem cells with differentiation ability, such as mesenchymal stem cells. The stem cells are co-cultured with specific bio-signaling molecules to induce the cells to begin signaling transduction, which drives the stem cell to differentiate into cells in specific tissue. Until now, the knowledge of culture and isolation of stem cell and the knowledge of bio-signaling molecules have been well developed. For scaffold, which provides the cell an environment to grow, relatively speaking, since factors such as the biocompatibility, cell adhesion, and cytotoxicity of the scaffold affects cell growth, which further affects the results of tissue preparation and tissue regeneration, the researchers in this field are still studying and improving the scaffold.

On the other hand, 3D printing has become more and more popular. The modeling can be completed by drawing software or three-dimensional scanner and then additively building up and curing thin layers step by step under computer control. The modeling can be finished without producing a real mold. 3D printing is highly efficient in preparation and avoids the need for mold preparation in advance, which may meet the demand of personalized medicine. Therefore, 3D bioprinting is invented. The molding methods of three-dimensional printing technology include photo-curing, laser sintering, melt extrusion, etc. The material is selected by the molding method. Among them, photo-curing method has high accuracy and has good surface properties of finished products, is applicable to a wide range of materials. Therefore, the industries which are more demanding of the finished products prefer to use photo-curing method. Photopolymer is used in photo-curing method. During the method, light is provided as excitation energy. A photoinitiator releases free radicals or cations after absorbing light, which further drives the monomers to polymerize into a polymer.

Accordingly, the purpose of the present disclosure is to combine the characteristics of the Gelatin methacrylate (GelMA) and the photopolymer, and further improve the structural strength and the biofunctionality of the materials based on the biocompatibility of the materials and the convenience of material formation. As a result, the present disclosure provides a photopolymer composition. When the photopolymer composition is applicable to the field of tissue engineering, compared to a conventional photopolymer, the photopolymer composition of the present disclosure has properties such as devoid of cytotoxicity, with better compressive strength and of providing bioactivity, thereby increasing its application to biomedical research and tissue repair.

SUMMARY OF INVENTION

In one aspect, the present disclosure provides a photopolymer composition comprising: 5 weight percent to 15 weight percent of gelatin methacrylate (GelMA), 0.1 weight percent to 5 weight percent of silanized biologically active additive, 0.1 weight percent to 5 weight percent of photoinitiator, and 75 weight percent to 95 weight percent of a solvent.

In one embodiment of the present disclosure, the silanized biologically active additive comprises silanized hydroxyapatite, silanized β-tricalcium phosphate (β-TCP) or silanized bio-active glass.

In one embodiment of the present disclosure, the photoinitiator comprises 2,2'-Azobis[2-Methyl-N-(2-hydroxyethyl)propionamide] (VA-086).

In one embodiment of the present disclosure, the photoinitiator can be excited by light with wavelength in a range from 400 nm to 800 nm so as to induce photopolymerization.

In one embodiment of the present disclosure, the solvent comprises water, phosphate buffered saline (PBS), conditioned media from cell line or cell culture media.

In another aspect, the photopolymer composition can be further used for preparing three-dimensional cell culture media.

In another aspect, the photopolymer composition can be further used for preparing tissue repair composition.

Furthermore, the present disclosure provides a method for preparing three-dimensional cell culture media. The method comprises steps of: mixing 5 weight percent to 15 weight percent of gelatin methacrylate (GelMA), 0.1 weight percent to 5 weight percent of silanized biologically active additive, 0.1 weight percent to 5 weight percent of photoinitiator into 75 weight percent to 95 weight percent of a solvent to form a mixture; adding at least one cell into the mixture; providing light to the mixture to induce photopolymerization of the mixture comprising the cell; and obtaining a three-dimensional cell culture media.

In one embodiment of the present disclosure, after the step of adding at least one cell into the mixture, photopolymerization is induced by a 3D printing apparatus to cure the mixture comprising the cell.

In one embodiment of the present disclosure, during the step of photopolymerization, the 3D printing apparatus provides light above the mixture and cures the mixture based on modeling information to form the three-dimensional cell culture media by sheet lamination.

In one embodiment of the present disclosure, the photoinitiator comprises 2,2'-Azobis[2-Methyl-N-(2-hydroxyethyl) propionamide] (VA-086).

In one embodiment of the present disclosure, the photoinitiator can be excited by light with wavelength in a range from 400 nm to 800 nm so as to induce photopolymerization.

In one embodiment of the present disclosure, the cell comprises a stem cell, a cancer stem cell, cell line, a somatic cell or a primary cell.

In one embodiment of the present disclosure, the silanized biologically active additive comprises silanized hydroxyapatite, silanized β-tricalcium phosphate (β-TCP) or silanized bio-active glass.

In one embodiment of the present disclosure, the solvent comprises water, phosphate buffered saline (PBS), conditioned media from cell line or cell culture media.

The three-dimensional cell culture media is prepared by the photopolymer composition through the method for preparing three-dimensional cell culture media of the present disclosure. During the process of the photopolymerization of the photopolymer composition, in addition to the crosslinkage between the monomers of gelatin methacrylate, covalent bonds are also formed between methacrylate group and silane group. As a result, the obtained three-dimensional cell culture media has improved compressive strength, has biocompatibility and without cytotoxicity at the same time. Furthermore, the three-dimensional cell culture media comprises hydroxyapatite, which is a biologically active material. Therefore, the three-dimensional cell culture media of the present disclosure can be broadly applicable to biomedical field and also applicable to tissue regeneration and tissue repair.

DETAILED DESCRIPTION OF THE INVENTION

Figure 1:
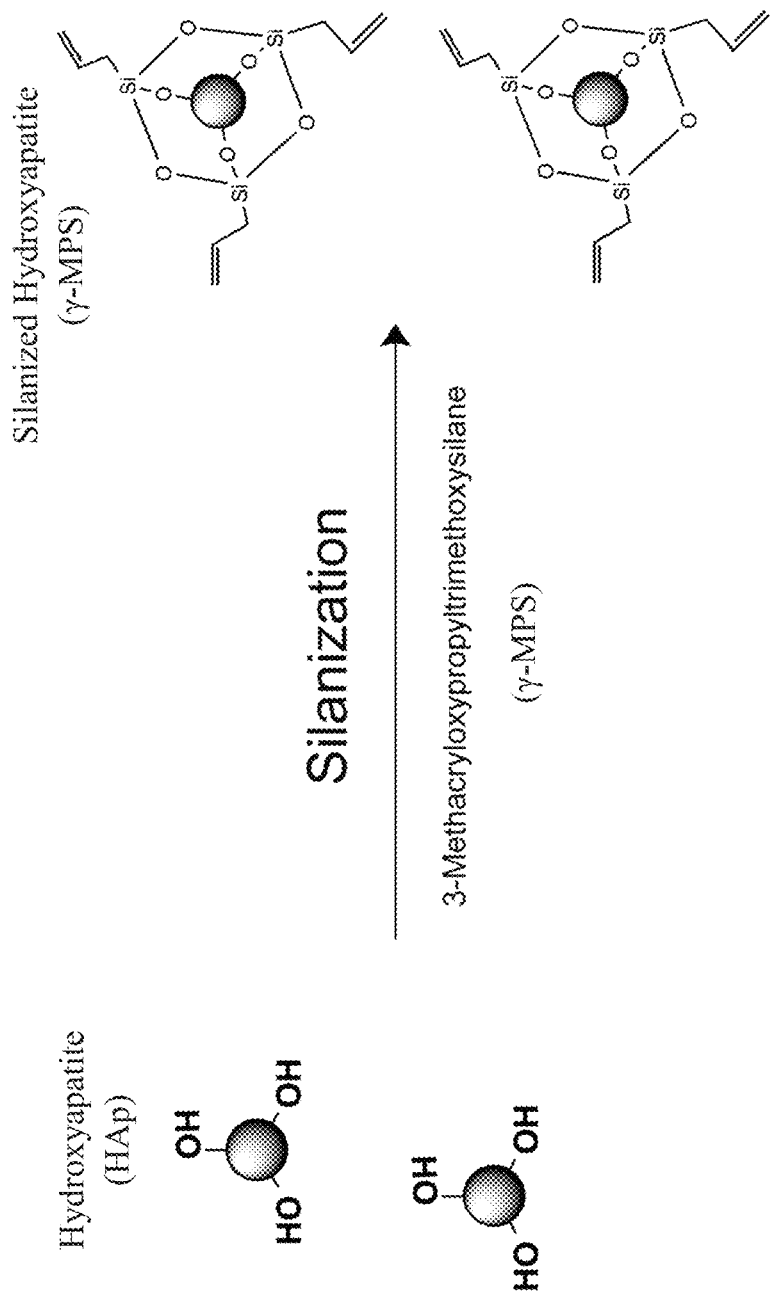
FIG. 1 is a diagram showing the silanization of hydroxyapatite by 3-Methacryloxypropyltrimethoxysilane (γ-MPS)

The following embodiments are given by way of illustration to help those skilled in the art fully understand the spirit of the present application. Hence, it should be noted that the present application is not limited to the embodiments herein and can be realized by various forms. Further, the drawings are not precise scale and components may be exaggerated in view of width, height, length, etc. Herein, the similar or identical reference numerals will denote the similar or identical components throughout the drawings.

Hydrogel is a material having both biocompatibility and biodegradability. However, since hydrogel is highly water-retentive, it is not liable to have fixed shape. Besides, hydrogel is very unstable at human body temperature, that is, hydrogel is difficult to maintain a gel or semi-solid form. In order to apply hydrogel to the field of tissue engineering, appropriate chemical modifications or specific chemical substances are needed to change the properties of hydrogel. Accordingly, the present disclosure provides a novel photopolymer composition comprising hydrogel as a main component. The photopolymer composition can be used for preparing three-dimensional cell culture media and is applicable to tissue repair. The present disclosure also provides a method for making a three-dimensional cell culture media by the photopolymer composition. Exemplary embodiments of the present application will be described in detail with reference to the accompanying drawings hereafter.

The photopolymer composition of the present disclosure comprises 5 weight percent to 15 weight percent of gelatin methacrylate (GelMA), 0.1 weight percent to 5 weight percent of silanized biologically active additive, 0.1 weight percent to 5 weight percent of photoinitiator, and 75 weight percent to 95 weight percent of a solvent.

In one embodiment, methacrylate (MA) is covalently bonded to gelatin form gelatin methacrylate (GelMA) having multiple carbon-carbon double bonds (C=C double bond). Besides, the silanized biologically active additive is an additive modified by silane group. The modification of silane group is to form multiple hydroxyl groups on the biologically active material. The biologically active additive may comprise material capable of activating or stimulating cells or tissues. In one embodiment, the biologically active additive comprises hydroxyapatite (HAp), β-tricalcium phosphate (β-TCP) or bioglass, and preferably, the biologically active additive comprises hydroxyapatite for undergoing silanization modification to form silanized hydroxyapatite (Si-HAp). Gelatin methacrylate can be prepared by any chemical reactions known in the art and the details will not be described herein. FIG. 1 is a diagram showing the silanization of hydroxyapatite. In one embodiment, 3-Methacryloxypropyltrimethoxysilane (γ-MPS) is used as a coupling agent to induce hydroxyapatite to undergo silanization to form silanized hydroxyapatite (Si-HAp).

As mentioned above, by using the photoinitiator, the gelatin methacrylate and the silanized hydroxyapatite are bonded to form polymer hydrogel. The photoinitiator releases free radicals or cations after absorbing light, which further drives the monomers to polymerize into a polymer. The selection of photoinitiator can be determined by the wavelength range of light and the applications of the polymer hydrogel afterwards. The wavelength range comprises infrared light in a range from 760 nm to 1000 nm, visible light in a range from 400 nm to 800 nm, and ultraviolet light in a range from 10 nm to 400 nm. The applications can be grouped in to biological need or non-biological need. In one embodiment, the photoinitiator comprises azo-initiator, which can be excited by visible light. In one embodiment, photoinitiator which can be excited by light in a range between 350 nm and 480 nm or photoinitiator which can be excited by blue light can be used. Furthermore, 2,2'-Azobis[2-Methyl-N-(2-hydroxyethyl)propionamide] (VA-086) is used, wherein 2,2'-Azobis[2-Methyl-N-(2-hydroxyethyl)propionamide] releases free radicals or cations to induce the gelatin methacrylate and the silanized hydroxyapatite to undergo photopolymerization after excited by blue light with a wavelength of 440 nm.

Figure 2:
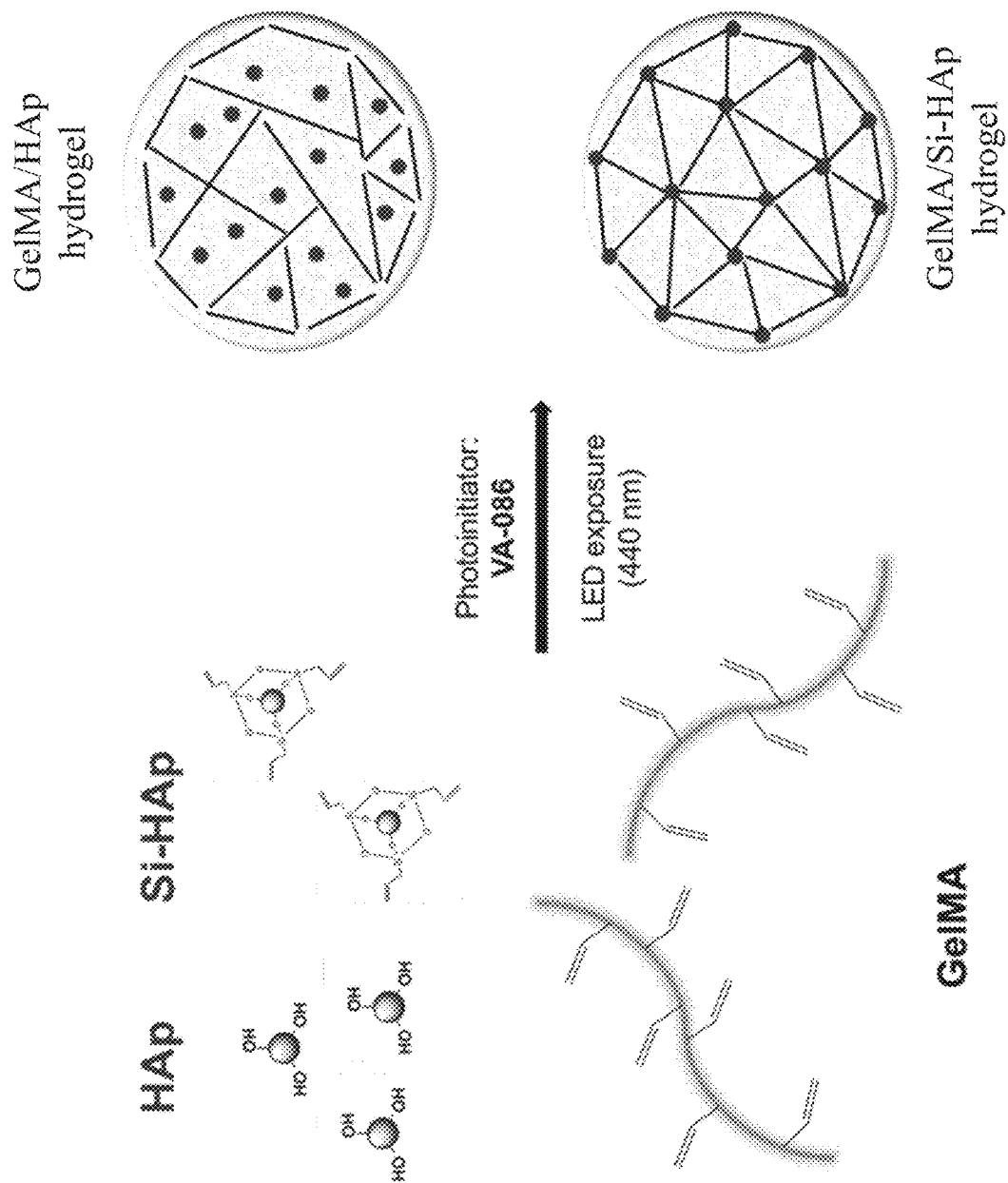
FIG. 2 is a diagram showing the structure of the polymer (GelMA/HAp) after the polymerization of the photopolymer composition of the present disclosure.
Figure 3:
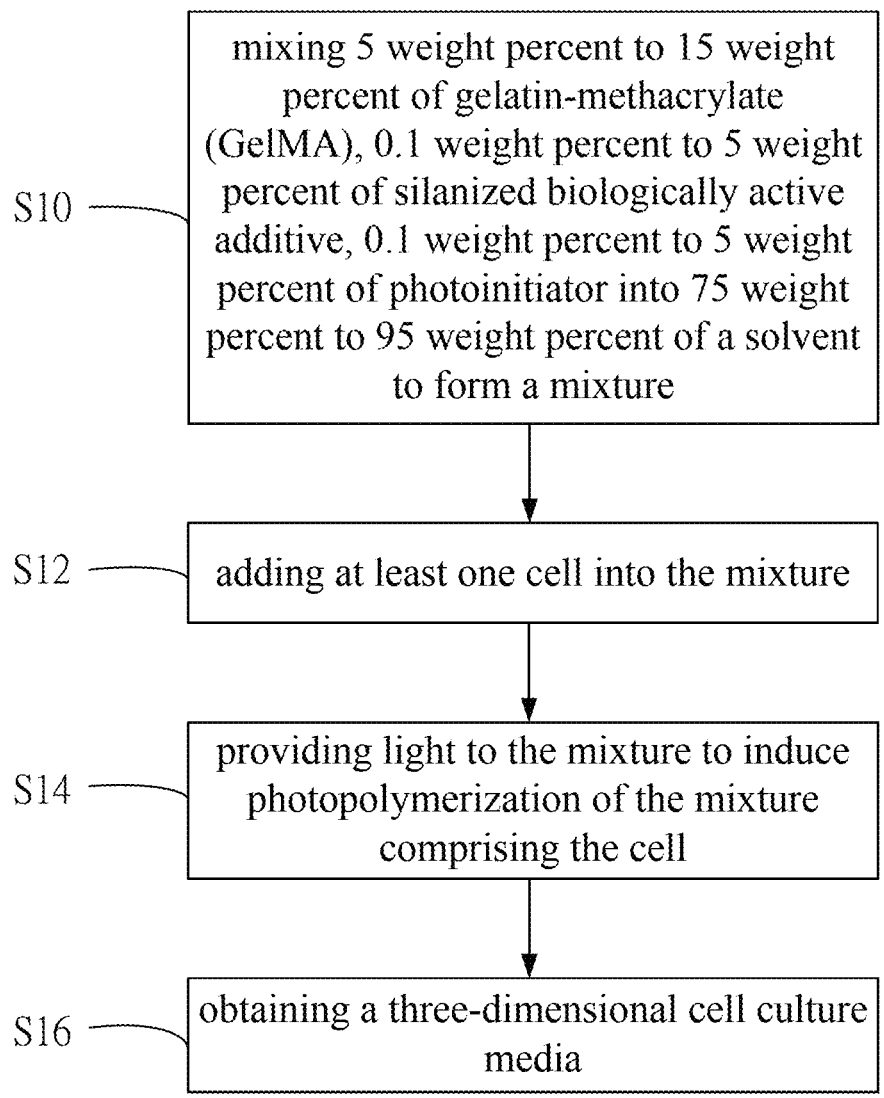
FIG. 3 is a process flow for the preparation of the three-dimensional cell culture media of the present disclosure.

Referring to FIGS. 1 and 2, in one embodiment of the present disclosure, during the process of photopolymerization of the gelatin methacrylate and silanized hydroxyapatite, in addition to the cross linkage between the monomers of gelatin methacrylate, carbon-carbon double bonds (C=C double bond) in the gelatin methacrylate are also bonded to the hydroxyl group in the silanized hydroxyapatite to form gelatin methacrylate/silanized hydroxyapatite hydrogel (GelMA/Si-HAp hydrogel). As shown in FIG. 2, compared to the chemical-bonding network of the gelatin methacrylate/hydroxyapatite hydrogel (GelMA/HAp hydrogel), the chemical-bonding network of gelatin methacrylate/silanized hydroxyapatite hydrogel (GelMA/Si-HAp hydrogel) is tighter. Accordingly, compared to a conventional gelatin methacrylate/hydroxyapatite hydrogel (GelMA/HAp hydrogel), the gelatin methacrylate/silanized hydroxyapatite hydrogel (GelMA/Si-HAp hydrogel) of the present disclosure has improved compressive strength and stability.

Referring to FIG. 4, three-dimensional cell culture media can be further prepared by the photopolymer composition of the present disclosure. The method for making the three-dimensional cell culture media comprises the steps of:

S10: mixing 5 weight percent to 15 weight percent of gelatin methacrylate (GelMA), 0.1 weight percent to 5 weight percent of silanized biologically active additive, 0.1 weight percent to 5 weight percent of photoinitiator, and 75 weight percent to 95 weight percent of a solvent to form a mixture;

S12: adding at least one cell into the mixture;

S14: providing light to the mixture to induce photopolymerization of the mixture comprising the cell;

S16: obtaining a three-dimensional cell culture media.

In the step S10, 5 weight percent to 15 weight percent of gelatin methacrylate (GelMA), 0.1 weight percent to 5 weight percent of silanized biologically active additive, 0.1 weight percent to 5 weight percent of photoinitiator are uniformly dissolved in 75 weight percent to 95 weight percent of the solvent. Specifically, the photopolymer composition can be put into water, phosphate buffered saline (PBS), conditioned media from cell line or cell culture media in advance and then an ultrasonic oscillator is used to uniformly dissolve the aggregation to obtain the mixture.

As mentioned in step S12, before the step of photopolymerization of the mixture, the method further comprises adding the cell into the mixture, uniformly mixing the cell and the mixture, and adding a suitable cell culture media for the selected cell to supply the cell with the material needed in cellular growth.

As mentioned in step S14, the method comprises the step of providing light to the mixture to excite the photoinitiator. Specifically, the light is visible light in a range from 400 nm to 800 nm. In one embodiment, blue light in a range from 350 nm to 480 nm is used to excite the photoinitiator. In a preferably embodiment, 2,2'-Azobis[2-Methyl-N-(2-hydroxyethyl)propionamide] (VA-086) is used as the photoinitiator. 2,2'-Azobis[2-Methyl-N-(2-hydroxyethyl)propionamide] releases free radicals or cations after excited by blue light with a wavelength of 440 nm. Furthermore, after releasing free radicals or cations, the gelatin methacrylate and the silanized hydroxyapatite are induced to undergo photopolymerization and cured with the cells together, which is called cell encapsulation. That is, the cells are fixed in the gelatin methacrylate/silanized hydroxyapatite hydrogel formed by photopolymerization of the mixture. As a result, a three-dimensional environment more similar to the animal body is provided for the cell to grow.

The cells comprise, but are not limited to, stem cells, cancer stem cells, cell lines, somatic cells or primary cells. Any cells that can live in vitro can be encapsulated in gelatin methacrylate/silanized hydroxyapatite hydrogel to carry out cell culture. On the other side, compared to the conventional method comprising a step of using ultraviolet light to induce the photopolymerization, since blue light is used to excite the photoinitiator to induce the photopolymerization in the present embodiment, damage to cells caused by the ultraviolet light during the photopolymerization can be avoided. Accordingly, the three-dimensional cell culture media prepared by the present disclosure is more suitable to the biomedical field or tissue regeneration for meeting the requirement of devoid of cytotoxic.

If the cells encapsulated in the gelatin methacrylate/silanized hydroxyapatite hydrogel are cell lines or cancer stem cells, a three-dimensional environment in the animal body can simulated in vitro for further study. If the cells encapsulated in the gelatin methacrylate/silanized hydroxyapatite hydrogel are stem cells with differentiation ability, the mixture comprising the cells can be directly applied to any animal tissues, and then light with specific wavelength is provided to irradiate the mixture to induce the photopolymerization to fix the mixture on the tissue. Accordingly, stem cells can differentiate into the cells the same as that of the tissue under the induction of the biologically active additive so as to undergo tissue repair.

Besides, different kinds of biologically active additives can be added into the mixture comprising the photopolymer composition. After the addition, the mixture can be directly applied to any animal tissues, and then three-dimensional cell culture media can be directly formed on the tissue after providing light to irradiate the mixture to undergo tissue repair. In one embodiment, silanized hydroxyapatite is added along with the stem cells to prepare the gelatin methacrylate/silanized hydroxyapatite hydrogel. The gelatin methacrylate/silanized hydroxyapatite hydrogel is applied to the area of damaged bone, and then the silanized hydroxyapatite, which has biologically active, induces stem cells to differentiate into the bone cells to undergo tissue repair.

In one embodiment of the present disclosure, before the step S14 of photopolymerization of the mixture comprising the photopolymer composition, the mixture is placed on a carrier of a 3D printing apparatus, and the light is adjusted to be over the mixture. In this step, a desired model can be completed by drawing software to obtain modeling information. After the modeling information is input into the 3D printing apparatus, the 3D printing apparatus can control the light in step S14 to move along x, y, or z axis based on the modeling information to provide light within a determined area so as to excite the photoinitiator in the photopolymer composition. Accordingly, the mixture comprising the photopolymer composition is gradually cured layer by layer to form the desired model to obtain the three-dimensional cell culture media.

Among the embodiments mentioned above, in order to meet the requirements of the three-dimensional cell culture and the application to the tissue repair, the mixture comprises 75 weight percent of aqueous solution or cell culture media. Accordingly, the mixture has good biocompatibility and is highly water-retentive. Relatively speaking, the mixture has higher fluidity before polymerization. As a result, light is configured to place over the mixture so as to carry out photopolymerization within a determined area, which removes the limitations of shaping the material when the light is configured under the material in the conventional way.

The three-dimensional cell culture media can be used to culture stem cells, cancer stem cells, cell line, somatic cells or primary cells in vitro so as to simulate three-dimensional environment in a living body for further cell experiments in biomedical research, such us cell growth test. Or, somatic cells or primary cells can be culture to obtain the substance secreted by the somatic cells or primary cells for further experiments or applications to the living bodies. On the other side, the three-dimensional cell culture encapsulating the stem cells can be directly applied to the animal tissue. For example, the three-dimensional cell culture media is directly applied to the area of damaged bone. As a result, under the stimulation of silanized hydroxyapatite, the stem cell is induced to differentiate into bone cells and facilitates cell growth, which is helpful for bone repair.

The following embodiments are given by way of illustration to help those skilled in the art fully understand the spirit of the present application. Hence, it should be noted that the present application is not limited to the embodiments herein and can be realized by various forms. Further, the drawings are not precise scale and components may be exaggerated in view of width, height, length, etc. Herein, the similar or identical reference numerals will denote the similar or identical components throughout the drawings.

The hydrogel of the present disclosure is provided by polymerization of gelatin methacrylate and silanized hydroxyapatite. The hydrogel of the present disclosure has improved mechanical strength. The biocompatibility of the hydrogel is further confirmed. Therefore, a photopolymer composition is provided to undergo photopolymerization by the irradiation of visible light. The photopolymer composition of the present disclosure can be applicable to tissue repair and biomedical research.

First Embodiment

Preparation of Gelatin Methacrylate Hydrogels

Gelatin methacrylate hydrogel is synthesized from gelatin (type A, 300 Bloom). The method for making the gelatin methacrylate hydrogels is described hereinafter. 5 grams of gelatin is added into 50 mL of phosphate buffered saline (PBS). The gelatin and the PBS are heated to a temperature of about 60° C. The gelatin is then dissolved completely in PBS. The gelatin solution is kept under stirring condition. A total volume of 5 mL of methacrylate anhydride (Sigma-Aldrich) is added into the gelatin solution at a rate of 0.1 mL/min. The reaction is conducted for 3 hours at a temperature of about 50° C. 250 mL of phosphate buffered saline at a temperature of about 50° C. is added to terminate the reaction. Modified polyethersulfone (PES) hollow fiber membrane (diameter kDa MWCO, Spectrum Labs, USA) is used to dialyze in distilled water at a temperature of about 50° C. for 24 hours to remove methacrylic acid. The obtained solution after dialysis is then dried for 3 days to form a spongiform-like product. The spongiform-like product is frozen at a temperature of about −80° C. Nuclear Magnetic Resonance (1H-NMR; Bruker, Ascend 400, USA) is used to analyze the ratio of methacrylation.

Second Embodiment

The Reaction of Silanization of Hydroxyapatite 5 grams of hydroxyapatite nano powder (Sigma-Aldric), 0.1 gram of n-propylamine and 0.5 gram of 3-Methacryloxypropyltrimethoxysilane (γ-MPS, Alfa Aesar) are added into 100 mL of cyclohexane (Sigma-Aldrich). The resulting solution is then agitated for approximately 30 minutes at a temperature of about 25° C. The resulting solution is then heated to a temperature of about 60° C. and kept for 30 minutes. Next, the resulting solution is placed into rotary evaporator under a temperature of about 60° C. to remove the solvent and then is heated at a temperature of about 90° C. for an hour. Finally, the powder is dried after being kept in a vacuum oven for 72 hours.

Figure 4A:
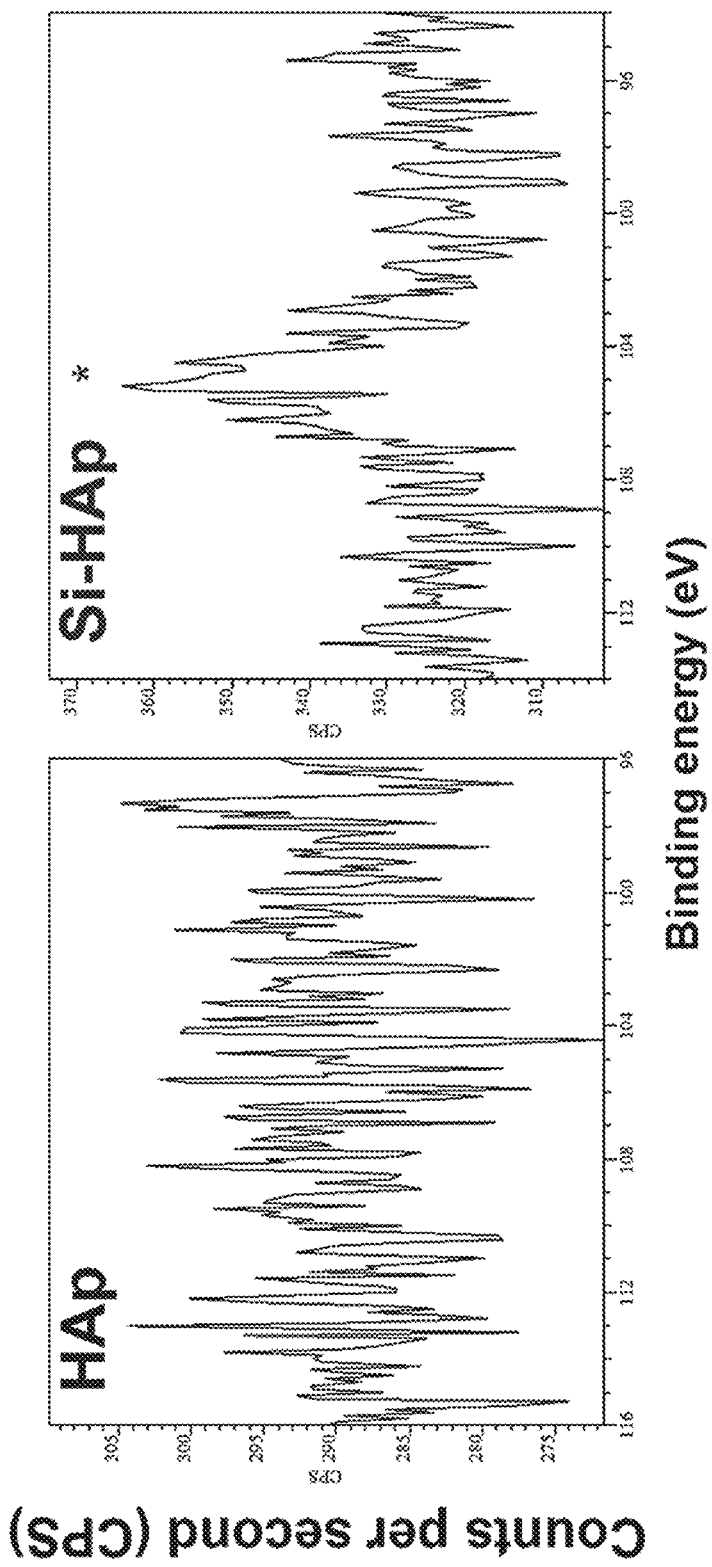
FIG. 4A is a X-ray photoelectron spectroscopy (XPS) spectrum of the hydroxyapatite and the silanized hydroxyapatite, wherein the peak that the symbol * indicate is Si 2p (Si—O), and the binding energy is about 104 eV.
Figure 4B:
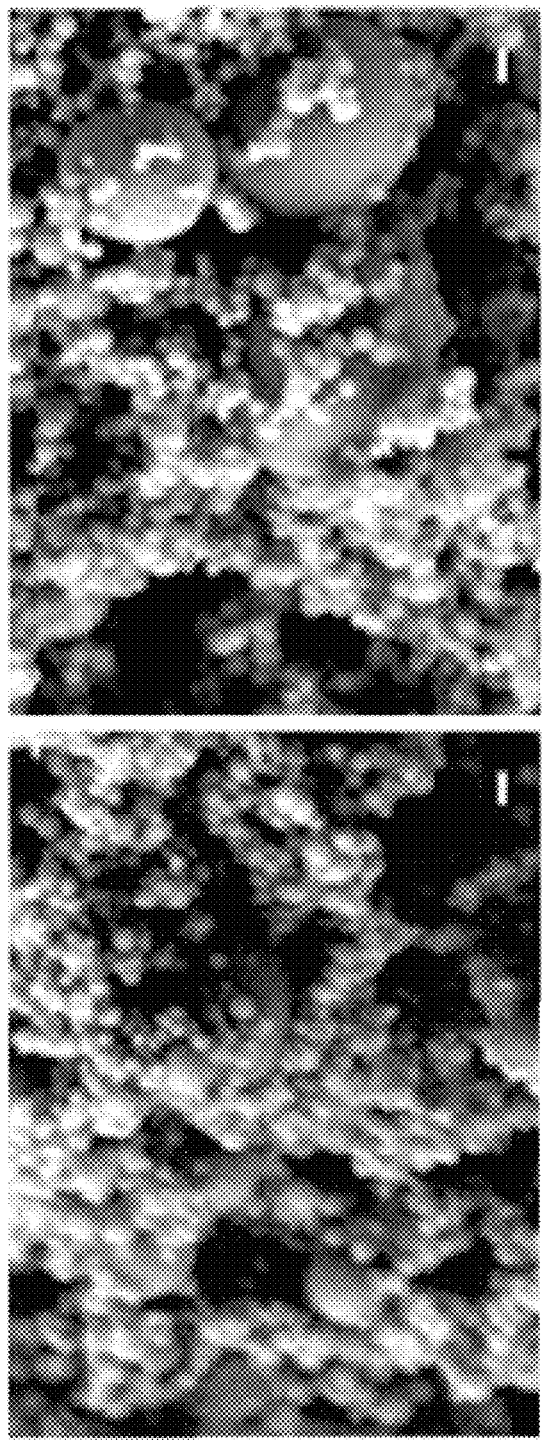
FIG. 4B are scanning electron microscopy (SEM) images of the hydroxyapatite and the silanized hydroxyapatite respectively, wherein the image is 50000× original magnification, and the scale is 100 nm.

After obtaining the silanized hydroxyapatite, X-ray photoelectron spectroscopy (XPS, ESCALAB 250, Thermo Scientific, USA) is used to analyze the composition. Referring to FIG. 4A, compared to the pre-modified hydroxyapatite on the left, the peak of Si with 2p orbital (Si 2p), which is indicated by the symbol *, can be seen. The binding energy of Si is about 104 eV. Besides, referring to FIG. 4B, scanning electron microscopy (JSM-7600F, JEOL, USA) is used to observe the morphology of surface modification. Silanization does not affect the morphology of hydroxyapatite. Either hydroxyapatite granular or silanized hydroxyapatite granular is still ball-like shape without deformation.

Third Embodiment

Preparation of Mixture of Gelatin Methacrylate/Silanized Hydroxyapatite (GelMA-Si-HAp)

Uniformly mixing 15 percent (w/v) of gelatin methacrylate, 1 to 3 percent (w/v) of silanized hydroxyapatite (Si- HAp) powder and 1 percent (w/v) of 2,2'-Azobis[2-Methyl-N-(2-hydroxyethyl)propionamide] (VA-086, Wako) as a photoinitiator by an ultrasonic oscillator at a frequency of 20 kHz. Specifically, aggregation should be avoided in the resulting mixture.

Fourth Embodiment

Mechanical Properties of Gelatin Methacrylate/Silanized Hydroxyapatite Hydrogel (GelMA-Si-HAap Hydrogel)

After obtaining the mixture of gelatin methacrylate/silanized hydroxyapatite from the third embodiment, blue light with a wavelength of 440 nm (8 mW/cm$^2$) is used to irradiate the mixture for 1 minute to excite the photoinitiator, which is VA-086 in the mixture, so as to induce photopolymerization. Gelatin methacrylate/silanized hydroxyapatite hydrogel without comprising any cells is obtained. The hydrogel is then analyzed to realize the properties of chemical bonds and mechanical properties.

Figure 5A:
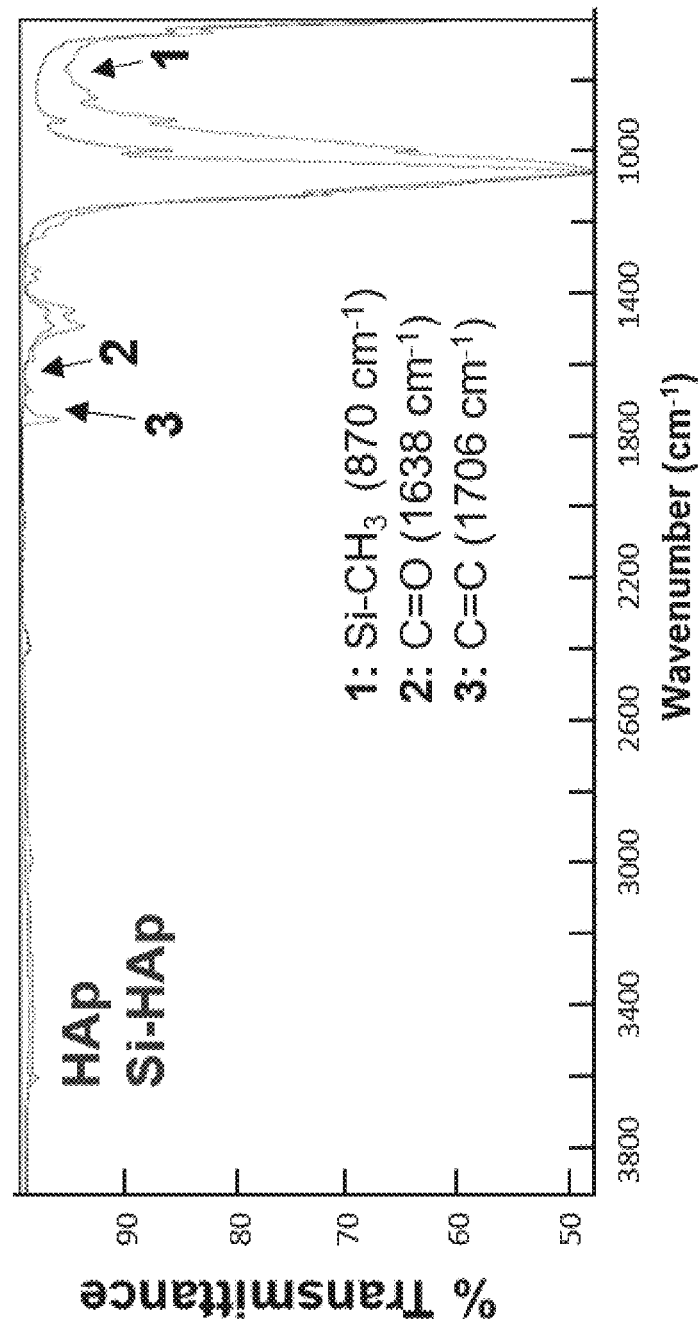
FIG. 5A is an attenuated total reflection Fourier-transform infrared spectroscopy (ATR-FTIR) spectrum of the hydroxyapatite and the silanized hydroxyapatite, wherein peak 1 is Si—CH3, peak 2 is C=O (1638 cm−1), and peak 3 is C=C (1706 cm−1)
Figure 5B:
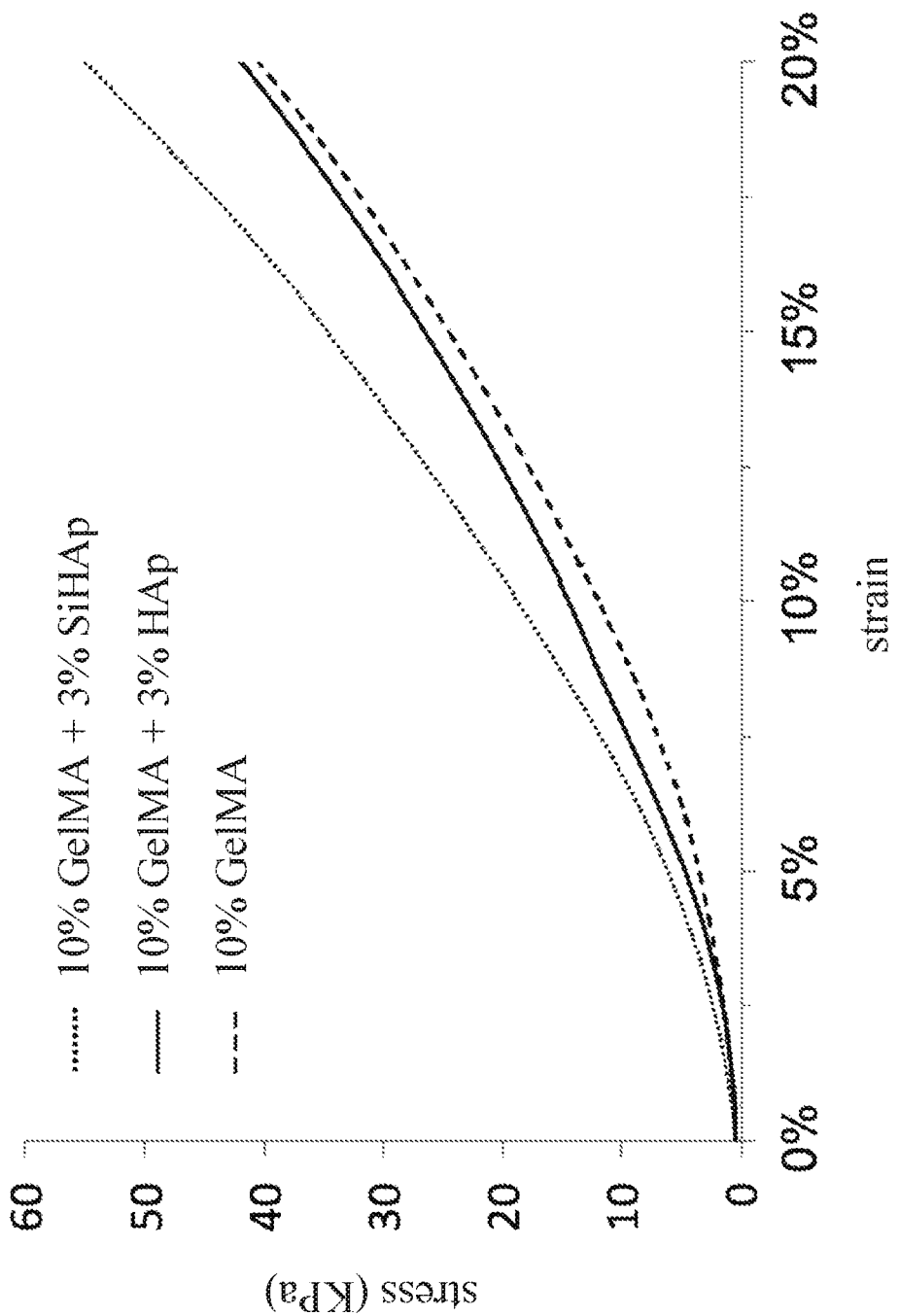
FIG. 5B is a chart showing the stress strain curves of 15 weight percent of gelatin methacrylate (GelMA), polymer of 15 weight percent of gelatin methacrylate (GelMA)/3 weight percent of hydroxyapatite and polymer of 15 weight percent of gelatin methacrylate (GelMA)/3 weight percent of silanized hydroxyapatite respectively.
Figure 5C:
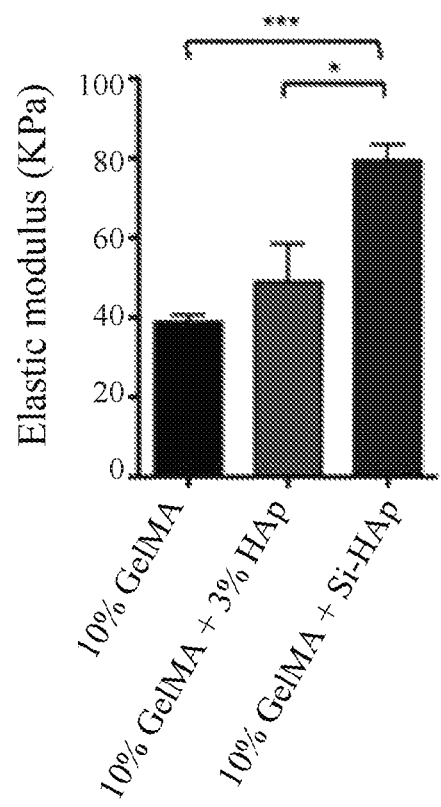
FIG. 5C is a chart showing the elastic modulus of 15 weight percent of gelatin methacrylate (GelMA), polymer of 15 weight percent of gelatin methacrylate (GelMA)/3 weight percent of hydroxyapatite and polymer of 15 weight percent of gelatin methacrylate (GelMA)/3 weight percent of silanized hydroxyapatite respectively.
Figure 5D:
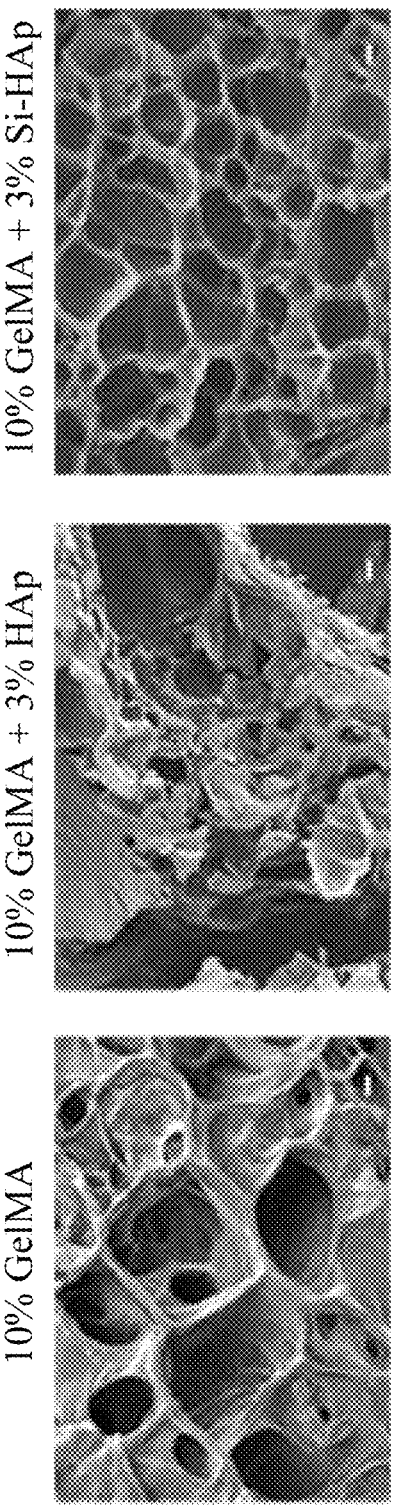
FIG. 5D are SEM images showing 10 weight percent of gelatin methacrylate (GelMA), polymer of 10 weight percent of gelatin methacrylate (GelMA)/3 weight percent of hydroxyapatite and polymer of 10 weight percent of gelatin methacrylate (GelMA)/3 weight percent of silanized hydroxyapatite respectively, wherein the scale is 100 μm, *, $p<0.05$, and ***, $p<0.001$.

Referring to FIG. 5A, Fourier-transform infrared spectroscopy (ATR-FTIR) is used to analyze hydroxyapatite and silanized hydroxyapatite (Si-HAp). In the spectrum of silanized hydroxyapatite (Si-HAp), peak number 1 is Si—CH3 (870 cm−1), peak number 2 is C═O (1706 cm−1), and peak 3 is C═C (1638 cm−1). Accordingly, covalent bonds are proved to be formed between the methacrylate group and the silane group, besides, with regard to the mechanical properties, as shown in FIG. 5B, which shows the stress strain curves. Compared to the hydrogel (GelMA-HAp) polymerizing with 3% hydroxyapatite (HAp), the hydrogel (GelMA-Si-HAp) polymerizing with 3% silanized hydroxyapatite (Si-HAp) has better compressive Strength. Referring to FIG. 5C, gelatin methacrylate/silanized hydroxyapatite hydrogel has better elastic modulus. Further referring to FIG. 5D, the network of the gelatin methacrylate/silanized hydroxyapatite hydrogel is tighter. From the results, the properties and the morphologies of the hydrogel mentioned above, the gelatin methacrylate/silanized hydroxyapatite hydrogel (GelMA-Si-HAp) obtained from polymerization of gelatin modified by methacrylate acid and the hydroxyapatite modified by silane group, in addition to the crosslinkage between the monomers of gelatin; covalent bonds are also formed between methacrylate group and silane group. As a result, the network of gelatin methacrylate/silanized hydroxyapatite hydrogel is tighter and more solid, and thus has improved compressive strength.

Fifth Embodiment

Gelatin Methacrylate/Silanized Hydroxyapatite Hydrogel (GelMA-HAp Hydrogels) is Prepared by 3D Printing Apparatus and Cells are Encapsulated in the Hydrogel Digital light processing projectors (D912HD, Vivitek, Taiwan) is vertically set up above the sample tank and at a distance of 10 cm. 1-3 mL of a mixture of gelatin methacrylate/silanized hydroxyapatite (GelMA-HAp) comprising 1 weight percent of VA-086 as a photoinitiator is provided. A cell number of 1×10$^6$/mL of MG63 cell line or a cell number of 1×10$^7$/mL of MSCs are mixed with the mixture. The resulting mixture is uniformly distributed in the culture tray (9.6 mm$^2$) On the other side, light-shielding are is designed in advance by Power Point (Microsoft, USA). The digital light processing projectors irradiates the area determined to be exposed from top to down for 40 seconds to induce photopolymerization within determined area of the gelatin methacrylate/silanized hydroxyapatite (GelMA-HAp) comprising the cells to polymerize into hydrogel. After irradiation, phosphate buffered saline is used to wash away the unreacted materials. Gelatin methacrylate/silanized hydroxyapatite hydrogel encapsulating the cells is obtained.

Sixth Embodiment

Figure 6:
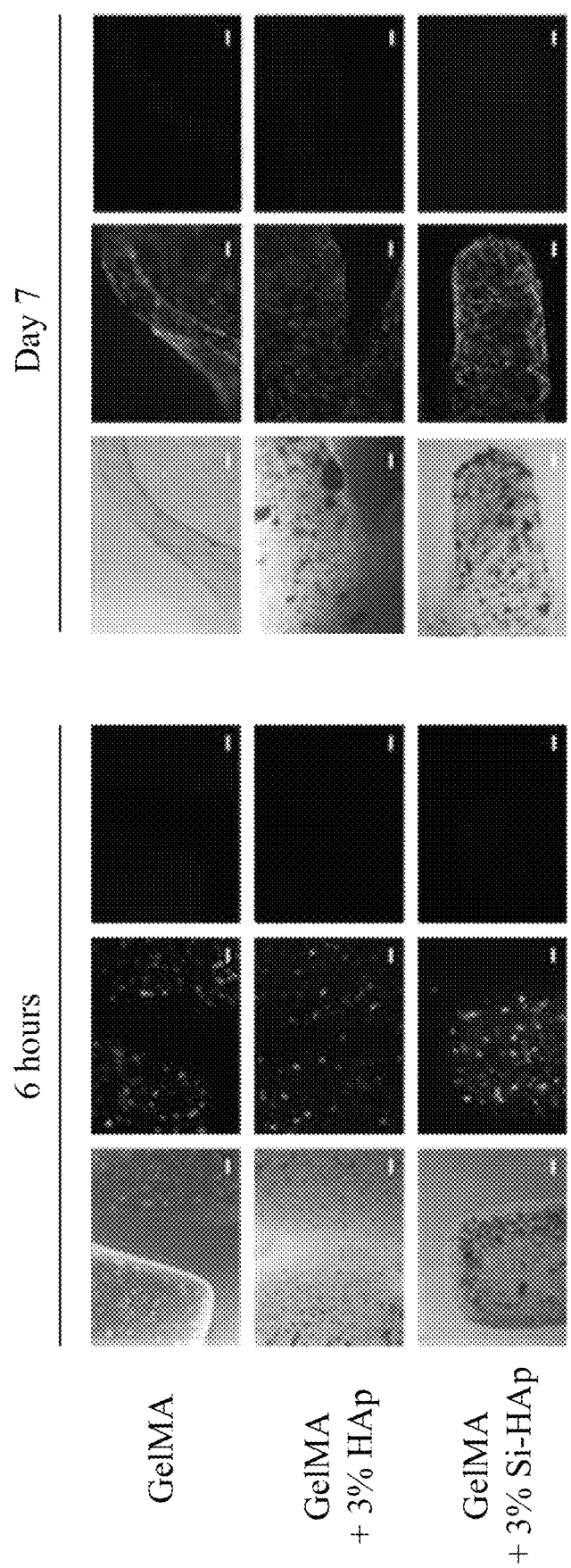
FIG. 6 are optical microscope results showing the cell growth rate test of the mesenchymal stem cell of human encapsulated by the three-dimensional cell culture media of the present disclosure, wherein the image on the left shows the result after 6 hours of culture, the image on the right shows the result after 7 days of culture, and the scale is 100 μm.

The Cell Growth Rate Test of the Mesenchymal Stem Cells of Human Encapsulated in the Gelatin Methacrylate/Silanized Hydroxyapatite Hydrogel After obtaining the methacrylate/silanized hydroxyapatite hydrogel encapsulating the cells from the fifth embodiment, the hydrogel is observed after 6 hours of culture and after 7 days of culture to analyze the cell grow capability. As shown in FIG. 6, most of the mesenchymal stem cells encapsulated in the hydrogel are still alive and distributed in the hydrogel after 7 days of culture. Accordingly, the gelatin methacrylate/silanized hydroxyapatite hydrogel of the present disclosure is devoid of cytotoxicity. Therefore, the gelatin methacrylate/silanized hydroxyapatite hydrogel of the present disclosure can be applicable to biomedical research or tissue repair.

From the results of the embodiments mentioned above, the present disclosure provides a photopolymer composition. During the polymerization of gelatin modified by methacrylate group and hydroxyapatite modified by silane group, in addition to the crosslinkage between the monomers of gelatin, covalent bonds are also formed between methacrylate group and silane group. As a result, the obtained gelatin methacrylate/hydroxyapatite hydrogel (GelMA/HAp hydrogel) has tighter chemical-bonding network. Accordingly, the hydrogel of the present disclosure has improved compressive strength and mechanical strength. Furthermore, the photopolymer composition of the present disclosure comprises photoinitiator excited by visible light. When the photopolymer composition is applied to the biomedicine research or tissue repair by the method for making the three-dimensional cell culture media of the present disclosure, compared to the conventional method, it is more convenient and efficient. Furthermore, the damage to the cells can be avoided. Accordingly, the photopolymer composition and the applications thereof and the method for making three-dimensional cell culture media from the photopolymer composition have advantages such as with improved mechanical strength and applicable to tissue repair by comprising biological active material.

The invention claimed is:
1. A photopolymer composition, comprising:
5 weight percent to 15 weight percent of gelatin methacrylate (GelMA);
0.1 weight percent to 5 weight percent of a silanized biologically active additive, wherein the silanized biologically active additive comprises silanized hydroxyapatite, silanized β-tricalcium phosphate (β-TCP), or silanized bio-active glass;
0.1 weight percent to 5 weight percent of photoinitiator; and
75 weight percent to 95 weight percent of a solvent.
2. The photopolymer composition according to claim 1, the photoinitiator comprises 2,2'-Azobis[2-Methyl-N-(2-hydroxyethyl) propionamide].

3. The photopolymer composition according to claim 1, wherein the photoinitiator can be excited by light with wavelength in a range from 400 nm to 800 nm so as to induce photopolymerization.

4. The photopolymer composition according to claim 1, wherein the solvent comprises water, phosphate buffered saline (PBS), conditioned media from cell line or cell culture media.

5. A three-dimensional cell culture media, comprising a photopolymer composition, wherein the photopolymer composition comprises:
    5 weight percent to 15 weight percent of gelatin methacrylate (GelMA);
    0.1 weight percent to 5 weight percent of silanized biologically active additive;
    0.1 weight percent to 5 weight percent of photoinitiator; and
    75 weight percent to 95 weight percent of a solvent,
    wherein the silanized biologically active additive comprises silanized hydroxyapatite, silanized β-tricalcium phosphate (β-TCP), or silanized bio-active glass.

6. A tissue repair composition, comprising the photopolymer composition according to claim 1.

7. A method for preparing a three-dimensional cell culture media, comprising steps of:
    mixing 5 weight percent to 15 weight percent of gelatin methacrylate (GelMA), 0.1 weight percent to 5 weight percent of a silanized biologically active additive, 0.1 weight percent to 5 weight percent of photoinitiator into 75 weight percent to 95 weight percent of a solvent to form a mixture, wherein the silanized biologically active additive comprises silanized hydroxyapatite, silanized β-tricalcium phosphate (β-TCP), or silanized bio-active glass;
    adding at least one cell into the mixture;
    providing light to the mixture to induce photopolymerization of the mixture comprising the cell; and
    obtaining a three-dimensional cell culture media.

8. The method according to claim 7, wherein after the step of adding at least one cell into the mixture, photopolymerization is induced by a 3D printing apparatus to cure the mixture comprising the cell.

9. The method according to claim 8, wherein during the step of photopolymerization, the 3D printing apparatus provides light above the mixture and cures the mixture based on modeling information to form the three-dimensional cell culture media by sheet lamination.

10. The method according to claim 7, the photoinitiator comprises 2,2'-Azobis[2-Methyl-N-(2-hydroxyethyl)propionamide] (VA-086).

11. The method according to claim 10, wherein the photoinitiator can be excited by light with wavelength in a range from 400 nm to 800 nm so as to induce photopolymerization.

12. The method according to claim 7, wherein the cell comprises a stem cell, a cancer stem cell, a cell line, a somatic cell or a primary cell.

13. The method according to claim 7, wherein the solvent comprises water, phosphate buffered saline (PBS), conditioned media from cell line or cell culture media.

* * * * *